(12) United States Patent
Yada et al.

(10) Patent No.: US 6,989,463 B2
(45) Date of Patent: Jan. 24, 2006

(54) METHOD FOR HANDLING HIGH-VISCOSITY SUBSTANCES

(75) Inventors: Shuhei Yada, Yokkaichi (JP); Yasushi Ogawa, Yokkaichi (JP); Kenji Takasaki, Yokkaichi (JP); Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/978,281

(22) Filed: Nov. 1, 2004

(65) Prior Publication Data

US 2005/0192462 A1 Sep. 1, 2005

Related U.S. Application Data

(63) Continuation of application No. PCT/JP04/12509, filed on Aug. 31, 2004.

(30) Foreign Application Priority Data

Feb. 26, 2004 (JP) .............................. 2004-051540

(51) Int. Cl.
   *C07C 57/02* (2006.01)
   *C07C 51/42* (2006.01)
   *C07C 69/34* (2006.01)
   *C07C 67/48* (2006.01)

(52) U.S. Cl. ...................... 560/201; 560/218; 562/598; 562/600

(58) Field of Classification Search ..................... None
See application file for complete search history.

(56) References Cited

U.S. PATENT DOCUMENTS 4,317,926 A * 3/1982 Sato et al. .................. 562/532

* cited by examiner

Primary Examiner—Paul A. Zucker
(74) Attorney, Agent, or Firm—Nixon & Vanderhye P.C.

(57) ABSTRACT

There is provided a method for handling high-viscosity substances discharged from a production process of acrylic acid or esters thereof by gas-phase catalytic oxidation, which method is improved such that upon transporting the high-viscosity substances in a molten state to a storage tank through a pipeline, the retention or clogging of the high-viscosity substances in the pipeline can be effectively prevented without adding a solvent thereto, resulting in smooth transportation thereof through the pipeline.

In the method for handling high-viscosity substances discharged from a production process of acrylic acid or esters thereof by gas-phase catalytic oxidation according to the present invention, when the high-viscosity substances are transported to a storage tank through a pipeline, contents of acrylic acid polymers and a polymerization inhibitor in the high-viscosity substances are controlled to not less than 40% by weight and not less than 4% by weight, respectively, and the high-viscosity substances are maintained at a temperature of not less than 110° C.

3 Claims, 1 Drawing Sheet

METHOD FOR HANDLING HIGH-VISCOSITY SUBSTANCES

This application is a continuation of PCT/JP04/12509 filed Aug. 31, 2004.

TECHNICAL FIELD

The present invention relates to a method for handling high-viscosity substances, and more particularly to a method for handling high-viscosity substances discharged from a production process of acrylic acid or esters thereof by gas-phase catalytic oxidation.

BACKGROUND ARTS

In the process for production of acrylic acid or esters thereof by gas-phase catalytic oxidation, a bottom liquid discharged from a distillation column, which contains acrylic acid polymers, is usually fed to a decomposition reactor and treated therein. More specifically, in the decomposition reactor, the acrylic acid polymers are decomposed into valuable substances such as acrylic acid, acrylic esters and alcohols and then are recovered together with other low-boiling components. Since the decomposition reaction is performed in the predetermined range owing to the operational conditions of the reactor, a certain amount of the acrylic acid polymers tend to remain undecomposed. The undecomposed acrylic acid polymers are concentrated upon separating the other low-boiling components therefrom. As a result, the acrylic acid polymers are in the form of high-viscosity substances, and discharged as a bottom liquid from the reactor. The thus discharged high-viscosity substances are transported as industrial wastes in a high-temperature molten state to a storage tank through a pipeline.

Also, in the case where the bottom liquid discharged from the distillation column is already in the form of high-viscosity substances having the same composition as that of the bottom liquid discharged from the decomposition reactor, the bottom liquid discharged from the distillation column is transported as industrial wastes to the storage tank through the pipeline.

However, it may be extremely difficult to transport the high-viscosity substances discharged from the decomposition reactor or distillation column through the pipeline. For example, upon transportation of the high-viscosity substances, there are caused various troubles such as retention and clogging thereof in the pipeline. In order to improve a transportability of such high-viscosity substances through the pipeline, there is known the method of adding a solvent such as water, alcohols, ethers and carboxylic acids to the high-viscosity substances (Japanese Patent Application Laid-open (KOKAI) No. 2000-290225).

However, the addition of the solvent to the high-viscosity substances leads to increase in amount of a liquid to be transported, resulting in uneconomical industrial production process. In addition, when a large amount of the solvent is added to the high-viscosity substances, the liquid temperature of the high-viscosity substances tends to be lowered, thereby sometimes causing retention or clogging thereof in the pipeline.

DISCLOSURE OF THE INVENTION

Problem to be Solved by the Invention

The present invention has been achieved for solving the above conventional problems. An object of the present invention is to provide a method for handling high-viscosity substances discharged from a production process of acrylic acid or esters thereof by gas-phase catalytic oxidation, which method is improved such that upon transporting the high-viscosity substances in a molten state to a storage tank through a pipeline, the retention or clogging of the high-viscosity substances in the pipeline can be effectively prevented without adding a solvent thereto, resulting in smooth transportation thereof through the pipeline.

Means for Solving the Problem

As a result of the present inventor's earnest studies concerning transportation of the high-viscosity substances through a pipeline, the following findings have been obtained. That is, although the high-viscosity substances are required to have a melting temperature of not less than 110° C. in order to transport the substances in a molten state, the high-viscosity substances (composed mainly of acrylic acid polymers) tend to be polymerized at such a temperature. Meanwhile, in the process for production of acrylic acid or esters thereof, a polymerization inhibitor is added thereto prior to a distillation operation therefor, so that the resultant high-viscosity substances tend to contain such a polymerization inhibitor in a concentrated state. Therefore, if the polymerization inhibitor in the high-viscosity substances is concentrated to a predetermined value to suitably utilize the actions thereof, it will be possible to effectively prevent the polymerization of the high-viscosity substances.

The present invention has been attained on the basis of the above findings. To accomplish the aim, in a first aspect of the present invention, there is provided a method for handling high-viscosity substances discharged from a process for producing acrylic acid or esters thereof by gas-phase catalytic oxidation, wherein upon transporting the high-viscosity substances to a storage tank through a pipeline, contents of acrylic acid polymers and a polymerization inhibitor in the high-viscosity substances are controlled to not less than 40% by weight and not less than 4% by weight, respectively, and the high-viscosity substances are maintained at a temperature of not less than 110° C.

Effect of the Invention

According to the method of the present invention, the high-viscosity substances discharged from a production process of acrylic acid or esters thereof by gas-phase catalytic oxidation, can be transported to a storage tank through a pipeline without occurrence of retention or clogging thereof in the pipeline.

PREFERRED EMBODIMENT FOR CARRYING OUT THE INVENTION

Figure 1:
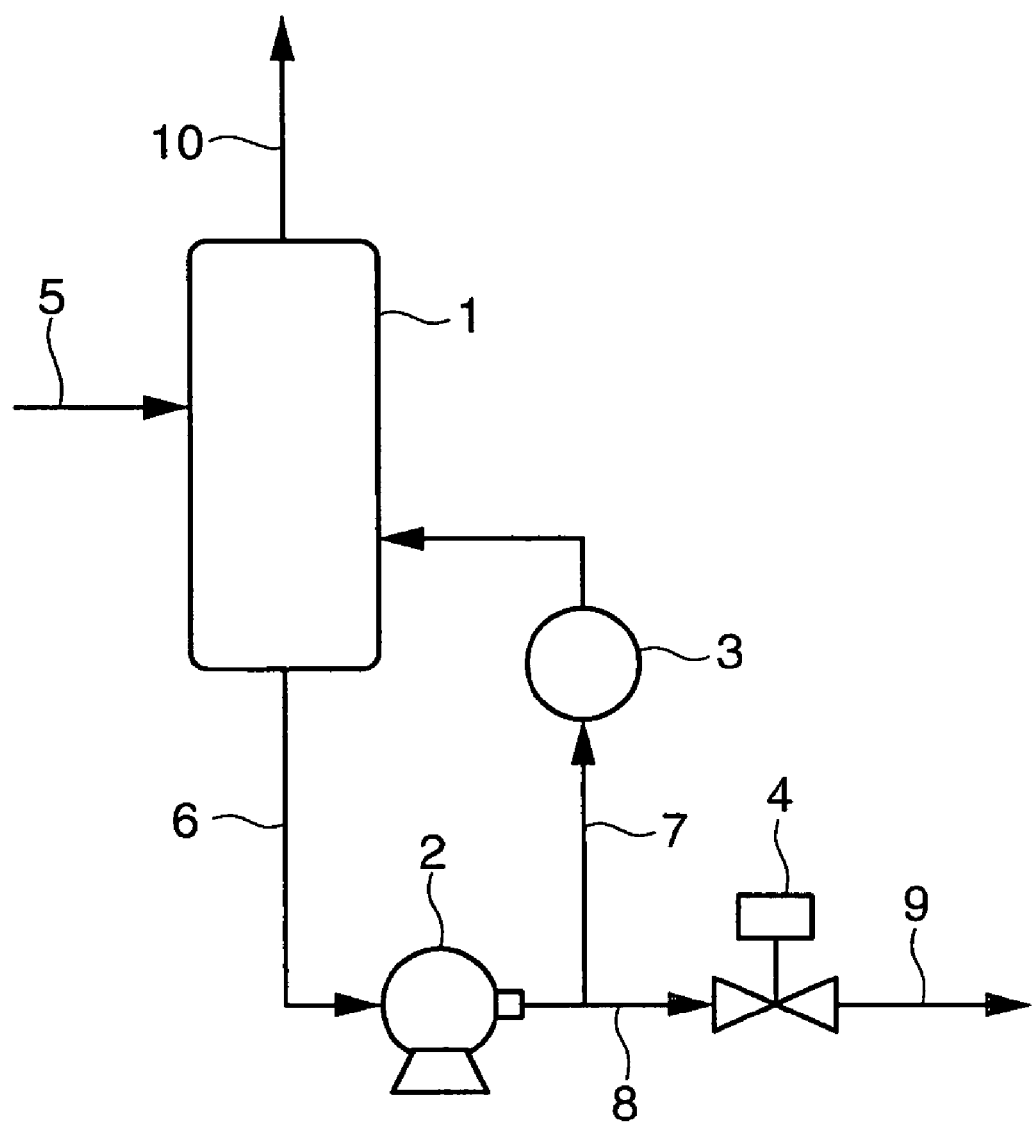
FIG. 1 is a flow diagram showing a process of decomposing a bottom liquid discharged from a distillation column used in the present invention.

The present invention is described in detail below. First, the general process for producing acrylic acid is explained. Acrylic acid can be produced by any of the following processes (1) to (3).

(1) A process comprising an oxidation step of subjecting propane, propylene and/or acrolein to gas-phase catalytic oxidation; a collection step of contacting the resultant acrylic acid-containing gas with water to collect acrylic acid in the form of an aqueous solution thereof; an extraction step of extracting acrylic acid from the thus obtained aqueous acrylic acid solution using an extraction solvent; a removing step, after distilling the obtained acrylic acid-containing solution to separate the solution into acrylic acid and the solvent, of removing low-boiling components from the obtained acrylic acid; and a purification step of further distilling the obtained acrylic acid.

(2) A process comprising an oxidation step of subjecting propane, propylene and/or acrolein to gas-phase catalytic oxidation; a collection step of contacting the resultant acrylic acid-containing gas with water to collect acrylic acid in the form of an aqueous solution thereof; an azeotropic separation step of distilling the thus obtained aqueous acrylic acid solution in the presence of an azeotropic agent in an azeotropic separation column and removing an acrylic acid-containing solution from a bottom of the column; a separation step of distilling the thus obtained acrylic acid-containing solution to remove acetic acid therefrom; and a purification step of further distilling the obtained acrylic acid.

(3) A process comprising an oxidation step of subjecting propane, propylene and/or acrolein to gas-phase catalytic oxidation; a collection/separation step of contacting the resultant acrylic acid-containing gas with an organic solvent to collect acrylic acid in the form of an organic solvent solution of acrylic acid, and simultaneously remove water and acetic acid therefrom; and a distillation step of distilling the thus obtained organic solvent solution of acrylic acid.

In any of the above methods, in the purification step thereof, there are obtained a top fraction containing acrylic acid and a bottom liquid containing acrylic acid polymers.

Although the details of the process for production of acrylic esters are omitted herein, the (acrylic esters may be produced, for example, by the process comprising an esterification reaction step of reacting acrylic acid with alcohol in the presence of a catalyst such as organic acids and cationic ion exchange resins, and a step of subjecting the thus obtained crude acrylic ester solution to extraction, evaporation and distillation in order to obtain the esters as a fraction distilled from a top of the column. In this distillation treatment, there is obtained a bottom liquid containing acrylic acid polymers and a polymerization inhibitor.

Examples of the obtained acrylic esters may include methyl acrylate, ethyl acrylate, butyl acrylate, isobutyl acrylate, tert-butyl acrylate, 2-ethylhexyl acrylate, 2-hydroxyethyl acrylate, 2-hydroxypropyl acrylate and methoxyethyl acrylate.

The method for handling the high-viscosity substances according to the present invention, is characterized in that upon transporting the high-viscosity substances to a storage tank through a pipeline, contents of acrylic acid polymers and a polymerization inhibitor in the high-viscosity substances are controlled to not less than 40% by weight and not less than 4% by weight, respectively, and the high-viscosity substances are maintained at a temperature of not less than 110° C.

The acrylic acid polymers described herein are compounds obtained by bonding two or more acrylic acid molecules, or two or more acrylic ester molecules to each other. Examples of the main component of the acrylic acid polymers may include Michael adducts.

Examples of the Michael adducts may include (i) Michael adducts of acrylic acid, (ii) Michael adducts of acrylic esters, and (iii) Michael adducts of alcohols. Specific examples of the Michael adducts (i) of acrylic acid may include acrylic acid dimers (hereinafter referred to merely as "dimers"), acrylic acid trimers (hereinafter referred to merely as "trimers"), acrylic acid tetramers (hereinafter referred to merely as "tetramers") and β-hydroxypropionic acid.

The Michael adducts (ii) of acrylic esters are compounds obtained by adding acrylic acid to the above acrylic esters such as alkyl esters having 2 to 8 carbon atoms or cycloalkyl esters of acrylic acid. Specific examples of the Michael adducts (ii) of acrylic esters may include β-acryloxypropionic acid esters such as methyl β-acryloxypropionate, ethyl β-acryloxypropionate, butyl β-acryloxypropionate and 2-ethylhexyl β-acryloxypropionate. The Michael adducts (iii) of alcohols are compounds obtained by adding alcohol or water to the acrylic esters. Specific examples of the Michael adducts (iii) of alcohols may include β-alkoxypropionic acid esters, esters of the dimers, trimers or tetramers, β-hydroxypropionic acid and β-hydroxypropionic acid esters.

Examples of the polymerization inhibitor for preventing polymerization of acrylic acid, acrylic esters or acrylic acid polymers may include copper acrylate, copper dithiocarbamates, phenol compounds and phenothiazine compounds.

Specific examples of the copper dithiocarbamates may include copper dialkyldithiocarbamates such as copper dimethyldithiocarbamate, copper diethyldithiocarbamate, copper dipropyldithiocarbamate and copper dibutyldithiocarbamate; copper cyclic alkylenedithiocarbamates such as copper ethylenedithiocarbamate, copper tetramethylenedithiocarbamate, copper pentamethylenedithiocarbamate and hexamethylenedithiocarbamate; and copper cyclic oxydialkylenedithiocarbamates such as oxydiethylenedithiocarbamate.

Specific examples of the phenol compounds may include hydroquinone, methoquinone, pyrogallol, catechol, resorcin, phenol and cresol. Specific examples of the phenothiazine compounds may include phenothiazine, bis-α-methylbenzyl)phenothiazine, 3,7-dioctyl phenothiazine and bis-(α,α'-dimethylbenzyl)phenothiazine. These compounds may be used singly or in combination of any two or more thereof.

One preferred embodiment of the method for handling the high-viscosity substances according to the present invention comprises the following sequential steps (A1) and (B) as explained by referring to FIG. 1. Meanwhile, FIG. 1 is a flow diagram showing a process of decomposing a bottom liquid discharged from a distillation column used in the present invention.

In the step (A1), the bottom liquid discharged from the distillation column is fed to a decomposition reactor, and decomposed therein such that contents of acrylic acid polymers and a polymerization inhibitor in the high-viscosity substances discharged from the decomposition reactor are controlled to not less than 40% by weight and not less than 4% by weight, respectively.

More specifically, the bottom liquid discharged from the distillation column is fed to the decomposition reactor (1) through a feed line (5). In the decomposition reactor, the acrylic acid polymers contained in the said bottom liquid are subjected to heat-decomposition treatment. The heat-decomposition treatment may be conducted such that contents of acrylic acid polymers and a polymerization inhibitor contained in the high-viscosity substances discharged from the decomposition reactor become to not less than 40% by weight and not less than 4% by weight, respectively. The decomposition reactor used may be of either column-type or vessel-type.

The bottom liquid may be fed by either a continuous method or an intermittent method (semi-continuous method). Of these methods, preferred is a continuous feeding method. The valuable substances such as acrylic acid, acrylic esters and alcohols as well as other low-boiling components, which are produced by decomposition of the acrylic acid polymers, are continuously discharged in a gaseous state through a recovery line (10). The thus discharged gases may be returned directly or in the form of a liquid after cooling, to the process for production of acrylic acid or esters thereof. Also, in the case of a column-type reactor, a part of the liquid obtained by cooling the gases discharged through the recovery line (10) may be returned as a refluxing liquid to a top of the decomposition reaction column (1).

In the column-type decomposition reactor, there may be used packing materials or trays. Examples of the packing material may include regular packing materials and irregular packing materials such as "SULZER PACKING" produced by Sulzer Brothers Limited, "SUMITOMO SULZER PACKING" produced by Sumitomo Heavy Industries Ltd., "MELAPACK" produced by Sumitomo Heavy Industries Ltd., "JEMPACK" produced by Grich Inc., "MONTZ-PACK" produced by Montz Inc., "GOODROLL PACKING" produced by Tokyo Special Wire Netting Co. Ltd., "HONEYCOMB PACK" produced NGK Insulators, Ltd., "IMPULSE PACKING" produced Nagaoka Corporation; and irregular packing materials such as "INTERLOCKS SADDLE" produced by Norton Inc., "TERALET" produced by Nittetu Chemical Engineering Ltd., "POLE RING" produced by BASF AG, "CASCADE MINI-RING" produced by Mass-Transfer Inc., and "FLEXI-RING" produced by JGC Corporation. These packing materials may be used in the combination of any two or more thereof, or may be used in combination with conventional trays.

Examples of the trays may include trays having a downcomer such as a bubble-cap tray, a perforate plate tray, a bubble tray, a super-flux tray and a max-flux tray, and trays having no downcomer such as a dual tray.

The vessel-type decomposition reactor may be constituted from a vessel solely, or a vessel provided therein with baffle plates, agitation blades, etc., if required.

The temperature of the decomposition reaction is usually in the range of 110 to 250° C., preferably 120 to 230° C. The decomposition reaction time may vary depending upon composition of the bottom liquid fed, use or non-use of the catalyst and decomposition reaction temperature. For example, when the decomposition reaction temperature is low, the decomposition reaction time is as relatively long as 10 to 50 hours, whereas when the decomposition reaction temperature is high, the decomposition reaction time is 30 min to 10 hours. The pressure used in the decomposition reaction may be either a reduced pressure or an ordinary pressure.

In the decomposition reaction, although only the bottom liquid may be treated, a mixture obtained by adding an acid catalyst and/or water to the bottom liquid may be treated for the purpose of promoting the decomposition reaction. As the acid catalyst, there may be mainly used sulfuric acid, phosphoric acid, methanesulfonic acid, p-toluenesulfonic acid, acids such as aluminum chloride, or Lewis acids. The acid catalyst and/or water may be fed to the decomposition reactor in the form of a mixture with the bottom liquid or separately from the bottom liquid. The polymers, polymerization inhibitor and catalyst which are contained in the bottom liquid discharged from the distillation column, are concentrated in the high-viscosity substances without being decomposed.

In the step (B), the high-viscosity substances discharged from the decomposition reactor are transported to a storage tank through a pipeline while maintaining a temperature of the high-viscosity substances at not less than 110° C.

More specifically, the high-viscosity substances discharged from the decomposition reactor (1) in the step (A1) are transported to the storage tank while maintaining a temperature of the high-viscosity substances at not less than 110° C. The high-viscosity substances discharged as a bottom liquid from the decomposition reactor (1) through a discharge line (6), contain not less than 40% by weight of acrylic acid polymers and not less than 4% by weight of the polymerization inhibitor. After feeding the thus discharged high-viscosity substances to a pump (2), a part thereof is fed to a heat exchanger (3) for heating through a line (7) and then returned back to the decomposition reactor (1), whereas a remainder thereof is fed through a line (8) and an intermittent removal control valve (4), and then transported to the storage tank through a pipeline (9).

The amount of the acrylic acid polymers contained in the high-viscosity substances is not less than 40% by weight, preferably not less than 45% by weight. When the content of the acrylic acid polymers is less than 40% by weight, the bottom liquid may fail to be sufficiently decomposed and, therefore, to be sufficiently concentrated, so that the amount of the liquid to be transported is uneconomically increased.

The amount of the polymerization inhibitor contained in the high-viscosity substances is not less than 4% by weight, preferably not less than 5% by weight. When the content of the polymerization inhibitor is less than 4% by weight, the high-viscosity substances tend to be polymerized during the transportation thereof.

The temperature of the high-viscosity substances being transported is not less than 110° C., preferably 110 to 200° C., more preferably 120 to 190° C. When the temperature of the high-viscosity substances during the transportation is less than 110° C., there tends to be caused retention or clogging thereof in the pipeline. Meanwhile, the high-viscosity substances obtained immediately after being discharged from the decomposition reactor lies within the range of 110 to 250° C. Therefore, since the difference in temperature between the high-viscosity substances and outside air is large, the high-viscosity substances tend to be cooled to a temperature of less than 110° C. during the transportation. As a result, the high-viscosity substances tend to be retained or clogged in the pipeline. Accordingly, the high-viscosity substances in the pipeline may be heated to maintain the temperature thereof at not less than 110° C.

Examples of the method of heating the high-viscosity substances may include (1) a method of flowing a heating medium (such as steam) through the pipeline constituted from a double tube, (2) a method of disposing a conduit through which a heating medium is flowed, along the pipeline; and (3) a method of disposing a heat exchanger for heating in the course of the pipeline.

Another preferred embodiment of the method for handling the high-viscosity substances according to the present invention comprises the following sequential steps (A2) and (B).

The step (A2) is constituted by a distillation step of purifying the acrylic acid or esters thereof such that contents of the acrylic acid polymers and the polymerization inhibitor in the high-viscosity substances discharged as a bottom liquid are not less than 40% by weight and not less than 4% by weight, respectively.

More specifically, the operation conditions of the distillation column are controlled such that the contents of the acrylic acid polymers and the polymerization inhibitor in the high-viscosity substances discharged as a bottom liquid therefrom are not less than 40% by weight and not less than 4% by weight, respectively.

In the step (B), the high-viscosity substances discharged from the distillation column are transported to a storage tank through a pipeline while maintaining a temperature of the high-viscosity substances at not less than 110° C. similarly to the step (B) described in the previous embodiment.

EXAMPLES

The present invention is described in more detail by Examples, but the Examples are only illustrative and not intended to limit the scope of the present invention.

Example 1

The bottom liquid discharged from a distillation column used in a production process of butyl acrylate by gas-phase catalytic oxidation method, which contained 22% by weight of butyl acrylate, 69% by weight of butyl β-butoxypropionate, 4% by weight of butyl acryloxypropionate, 2% by weight of butyl β-hydroxypropionate, 2% by weight of hydroquinone and 1% by weight of methoquinone was used as a raw material.

In the step (A1), the above bottom liquid was continuously fed at a rate of 580 kg/h to the decomposition reactor (1) through the line (5). As the decomposition reactor (1), there was used a column-type decomposition reactor made of hastelloy C having an outer diameter of 600 mm and a length of 1,800 mm. Also, a 1 wt % sulfuric acid aqueous solution as a decomposition reaction catalyst was fed to the decomposition reactor at a rate of 58 kg/h (equivalent to 10% by weight based on the weight of the raw material fed), and the decomposition reaction was conducted under a pressure of 100 kPa at 190° C. for a residence time of one hour.

Valuable substances composed mainly of butyl acrylate were recovered from a top of the decomposition reactor (1) at a rate of 449.5 kg/h. Whereas, high-viscosity substances having such a composition as shown in Table 1 were intermittently discharged from a bottom of the decomposition reactor at a rate of 188.5 kg/h.

TABLE 1

| Components | Amount (wt %) |
|---|---|
| Butyl acrylate | 11.7 |
| Butyl β-butoxypropionate | 70.4 |
| Butyl acryloxypropionate | 4 |
| Butyl β-hydroxypropionate, | 0.7 |
| Hydroquinone | 6.2 |
| Methoquinone | 3.1 |
| Butanol | 0.8 |
| Sulfuric acid | 3.1 |

It was confirmed that the thus obtained high-viscosity substances contained about 77% by weight of Michael adducts and about 10% by weight of the polymerization inhibitor.

The thus discharged high-viscosity substances were transported to a storage tank disposed 1,000 m apart from the decomposition reactor through a ¾Bφ SUS304 pipeline (inner diameter: 22.2 mm) at a rate of 0.2 m/s. A ½B CS conduit (steam trace) through which 3 KG steam was flowed, was disposed along an outside of the pipeline, so that the liquid within the pipeline was heated to a temperature of 130 to 135° C. Under the above conditions, the reaction system was continuously operated for 6 months. As a result, it was confirmed that the pipeline was free from clogging.

Comparative Example 1

The same procedure as defined in Example 1 was conducted except that the supply of steam through the CS conduit disposed along the pipeline was interrupted, so that the liquid temperature in the pipeline was in the range of 50 to 70° C. After initiation of the operation, it gradually became difficult to transport the high-viscosity substances through the pipeline. Therefore, after two weeks from initiation of the operation, the transportation was interrupted to inspect an inside of the pipeline. As a result, it was confirmed that the pipeline was clogged.

Example 2

The bottom liquid discharged from a distillation column used in a process for producing acrylic acid by gas-phase catalytic oxidation method, which contained 46.0% by weight of acrylic acid, 10.0% by weight of maleic acid, 42.4% by weight of an acrylic acid dimer (acryloxypropionic acid), 0.9% by weight of hydroquinone and 0.7% by weight of phenothiazine was used as a raw material.

Using the same decomposition reactor as used in Example 1, the above bottom liquid was continuously fed at a rate of 580 kg/h to the decomposition reactor (1) through the line (5), and the decomposition reaction was conducted under a pressure of 72 kPa at 190° C. for a residence time of one hour.

Valuable substances composed mainly of acrylic acid were recovered from a top of the decomposition reactor (1) at a rate of 449.5 kg/h. Whereas, high-viscosity substances having such a composition as shown in Table 2 were intermittently discharged from a bottom of the decomposition reactor at a rate of 130.5 kg/h.

TABLE 2

| Components | Amount (wt %) |
|---|---|
| Acrylic acid | 9 |
| Maleic acid | 14 |
| Acrylic acid dimer (acryloxypropionic acid) | 69.5 |
| Hydroquinone | 4.0 |
| Phenothiazine | 3.1 |
| Oligomers and Polymers | 0.4 |

It was confirmed that the thus obtained high-viscosity substances contained about 70% by weight of Michael adducts and about 7% by weight of the polymerization inhibitor.

The thus discharged high-viscosity substances were transported to a storage tank disposed 1,200 m apart from the decomposition reactor through a ¾Bφ SUS316 pipeline (inner diameter: 22.2 mm) at a rate of 0.4 m/s. The pipeline had a double tube structure whose outer tube was supplied with 2 KG steam, so that the liquid within the pipeline was heated to a temperature of 120 to 125° C. Under the above conditions, the reaction system was continuously operated for 4 months. As a result, it was confirmed that the pipeline was free from clogging.

Comparative Example 2

The same procedure as defined in Example 2 was conducted except that the supply of steam through the outer tube of the double-tube pipeline was interrupted, so that the liquid temperature in the pipeline was in the range of 70 to 80° C.

After initiation of the operation, it gradually became difficult to transport the high-viscosity substances through the pipeline. Therefore, after one week from initiation of the operation, the transportation was interrupted to inspect an inside of the pipeline. As a result, it was confirmed that the pipeline was clogged.

Example 3

The high-viscosity substances as a bottom liquid discharged from a distillation column used in a production process of ethyl acrylate by gas-phase catalytic oxidation method which had such a composition as shown in Table 3, were transported to a storage tank disposed 800 m apart from the distillation column through a ¾Bφ SUS316 pipeline (inner diameter: 22.2 mm) at a rate of 0.3 m/s. It was confirmed that the thus obtained high-viscosity substances contained about 70% by weight of Michael adducts and about 6% by weight of the polymerization inhibitor. The pipeline had a double tube structure whose outer tube was supplied with 2 KG steam, so that the temperature of the liquid within the pipeline was raised 120 to 125° C. Under the above conditions, the reaction system was continuously operated for 4 months. As a result, it was confirmed that the pipeline was free from clogging.

TABLE 3

| Components | Amount (wt %) |
|---|---|
| Acrylic acid | 16 |
| Ethyl ethoxypropionate | 14 |
| Ethoxypropionic acid | 39 |
| Ethyl acrylate dimer (ethyl acryloxypropionate) | 9 |
| Acrylic acid dimer (acryloxypropionic acid) | 7 |
| Hydroquinone | 6 |
| Oligomers and Polymers | 0.2 |

Comparative Example 3

The same procedure as defined in Example 3 was conducted except that the supply of steam through the outer tube of the double-tube pipeline was interrupted, so that the liquid temperature in the pipeline was in the range of 50 to 70° C. After initiation of the operation, it gradually became difficult to transport the high-viscosity substances through the pipeline. Therefore, after one week from initiation of the operation, the transportation was interrupted to inspect an inside of the pipeline. As a result, it was confirmed that the pipeline was clogged.

What is claimed is:

1. A method for handling high-viscosity substances discharged from a production process of acrylic acid or esters thereof by gas-phase catalytic oxidation, wherein upon transporting the high-viscosity substances to a storage tank, contents of acrylic acid polymers and a polymerization inhibitor in the high-viscosity substances are controlled to not less than 40% by weight and not less than 4% by weight, respectively, and the high-viscosity substances are maintained at a temperature of not less than 110° C.

2. A method according to claim 1, comprising the following sequential steps (A1) and (B):
   (A1) feeding a bottom liquid discharged from a distillation column to a decomposition reactor to decompose the bottom liquid such that contents of acrylic acid polymers and a polymerization inhibitor in the high-viscosity substances discharged from the decomposition reactor become to not less than 40% by weight and not less than 4% by weight, respectively; and
   (B) transporting the high-viscosity substances discharged from the decomposition reactor to the storage tank through a pipeline while maintaining a temperature of the high-viscosity substances at not less than 110° C.

3. A method according to claim 1, comprising the following sequential steps (A2) and (B):
   (A2) purifying the acrylic acid or esters thereof by distillation such that contents of acrylic acid polymers and a polymerization inhibitor in the high-viscosity substances discharged as a bottom liquid from a distillation column become to not less than 40% by weight and not less than 4% by weight, respectively; and
   (B) transporting the high-viscosity substances discharged from the distillation column to the storage tank through a pipeline while maintaining a temperature of the high-viscosity substances at not less than 110° C.

* * * * *